US00PP28470P3

(12) United States Plant Patent
Larse

(10) Patent No.: US PP28,470 P3
(45) Date of Patent: Oct. 3, 2017

(54) STRAWBERRY PLANT NAMED 'FLAME'

(50) Latin Name: *Fragaria×ananassa*
Varietal Denomination: Flame

(71) Applicant: John Larse, Aptos, CA (US)

(72) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 14/545,267

(22) Filed: Apr. 14, 2015

(65) Prior Publication Data

US 2016/0309633 P1 Oct. 20, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Keith Robinson
(74) *Attorney, Agent, or Firm* — Cooley LLP

(57) ABSTRACT

The present invention provides a new and distinct strawberry variety designated as 'Flame' (a.k.a. '108229').

6 Drawing Sheets

Latin name of the genus and species: *Fragaria×ananassa.*
Varietal denominations: 'Flame'.

BACKGROUND OF THE INVENTION

The present invention relates to new and distinct day-neutral strawberry variety designated as 'Flame' (a.k.a. '108229').

'Flame' (a.k.a. '108229') is the result of a controlled-cross between a female parent cultivar designated 102850 and a male parent cultivar designated 106734 (both unpatented, proprietary cultivars) made by the Inventor and was first fruited in Watsonville, Calif. growing fields. Following selection and during testing, the plant was originally designated '108229' and subsequently named 'Flame'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar was stable and reproduces true to type in successive generations of asexual reproduction.

BRIEF SUMMARY OF THE INVENTION

This invention relates to new and distinctive strawberry cultivar designated as 'Flame'. This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish strawberry variety 'Flame' from known strawberry varieties. In addition, this new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The fruit produced by this new cultivar is attractive and of excellent quality.

DESCRIPTION OF THE DRAWINGS

The accompanying color photographs depict various characteristics of the cultivar as nearly true as possible to make color reproductions. Dormant bare root plants of 'Flame' were planted on October, Year 1, and the photos were taken around May to June, Year 2.

DETAILED DESCRIPTION OF THE INVENTION

'Flame' (a.k.a. '108229')

Figure 1:
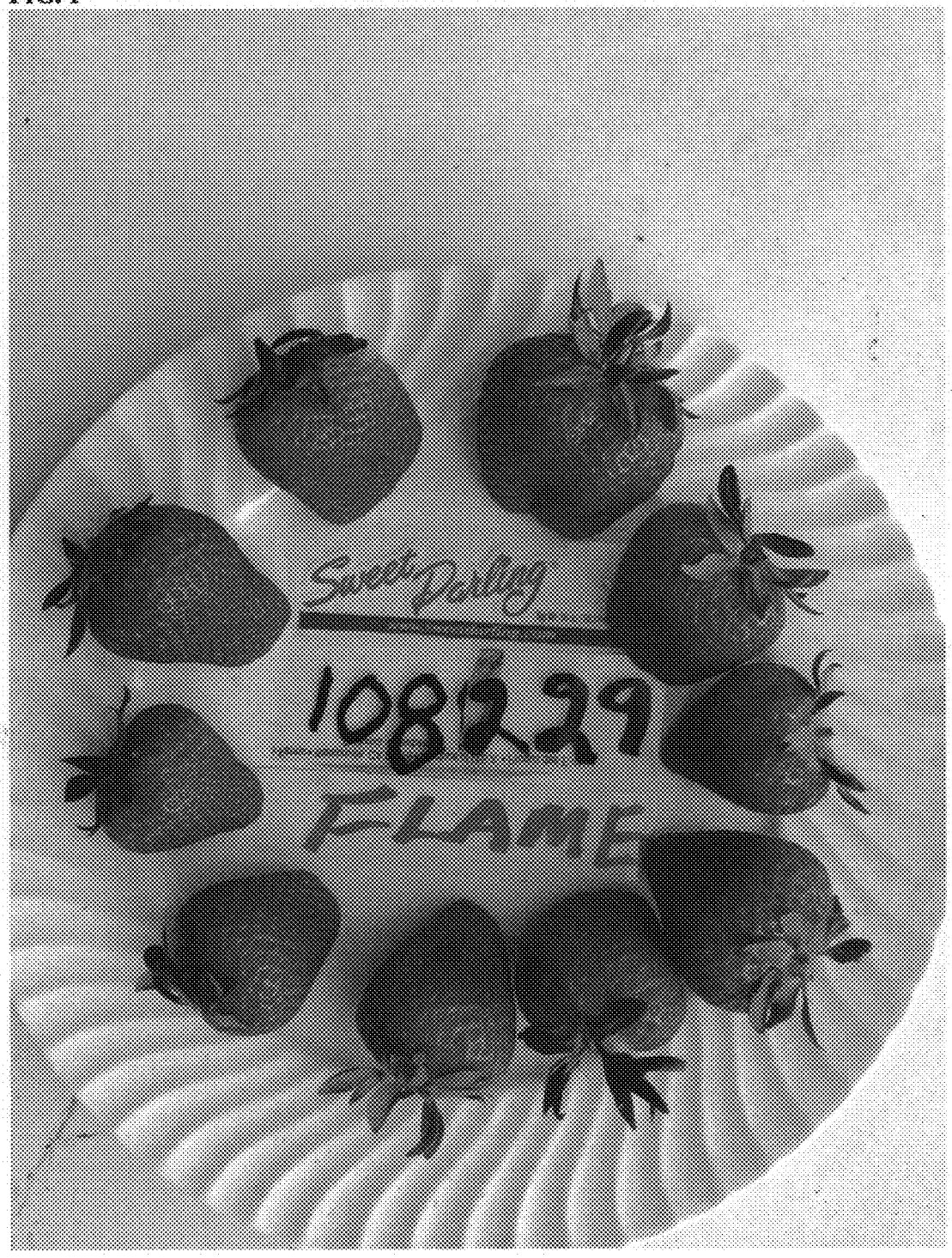
FIG. 1 shows ripe and near-ripe fruits of 'Flame' in May.
Figure 2:
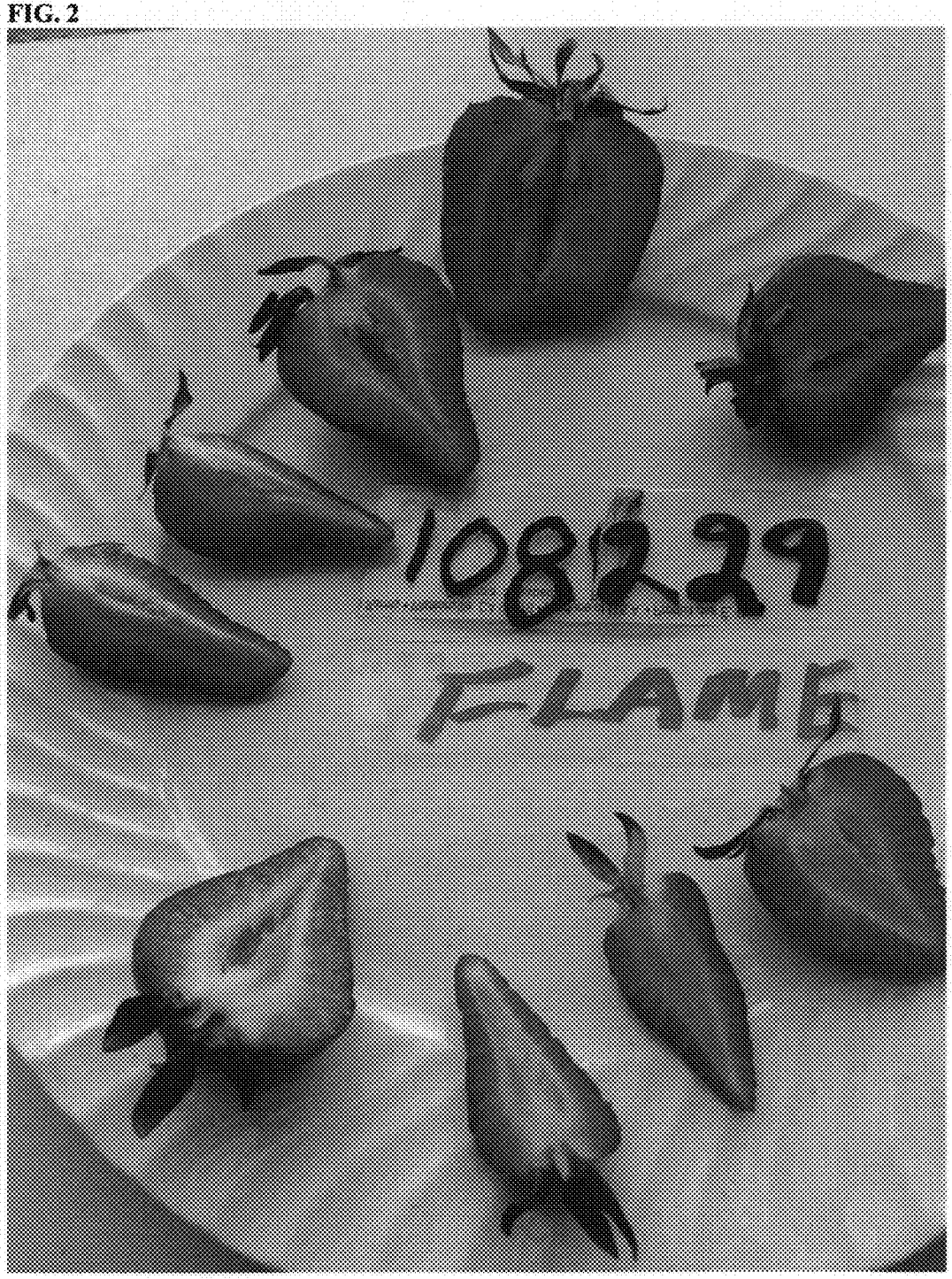
FIG. 2 shows sliced fruits of 'Flame'.
Figure 3:
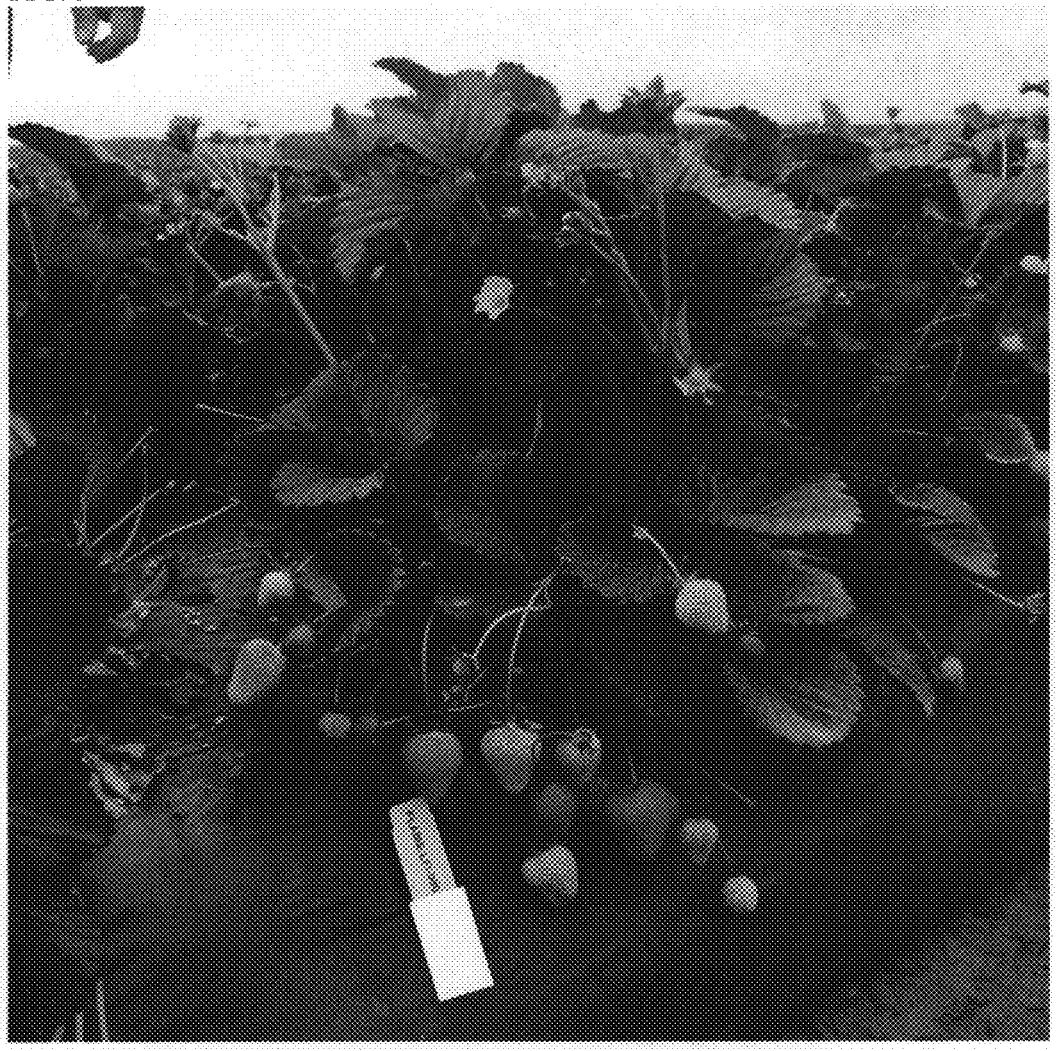
FIG. 3 shows 'Flame' plants growing in the field.
Figure 4:
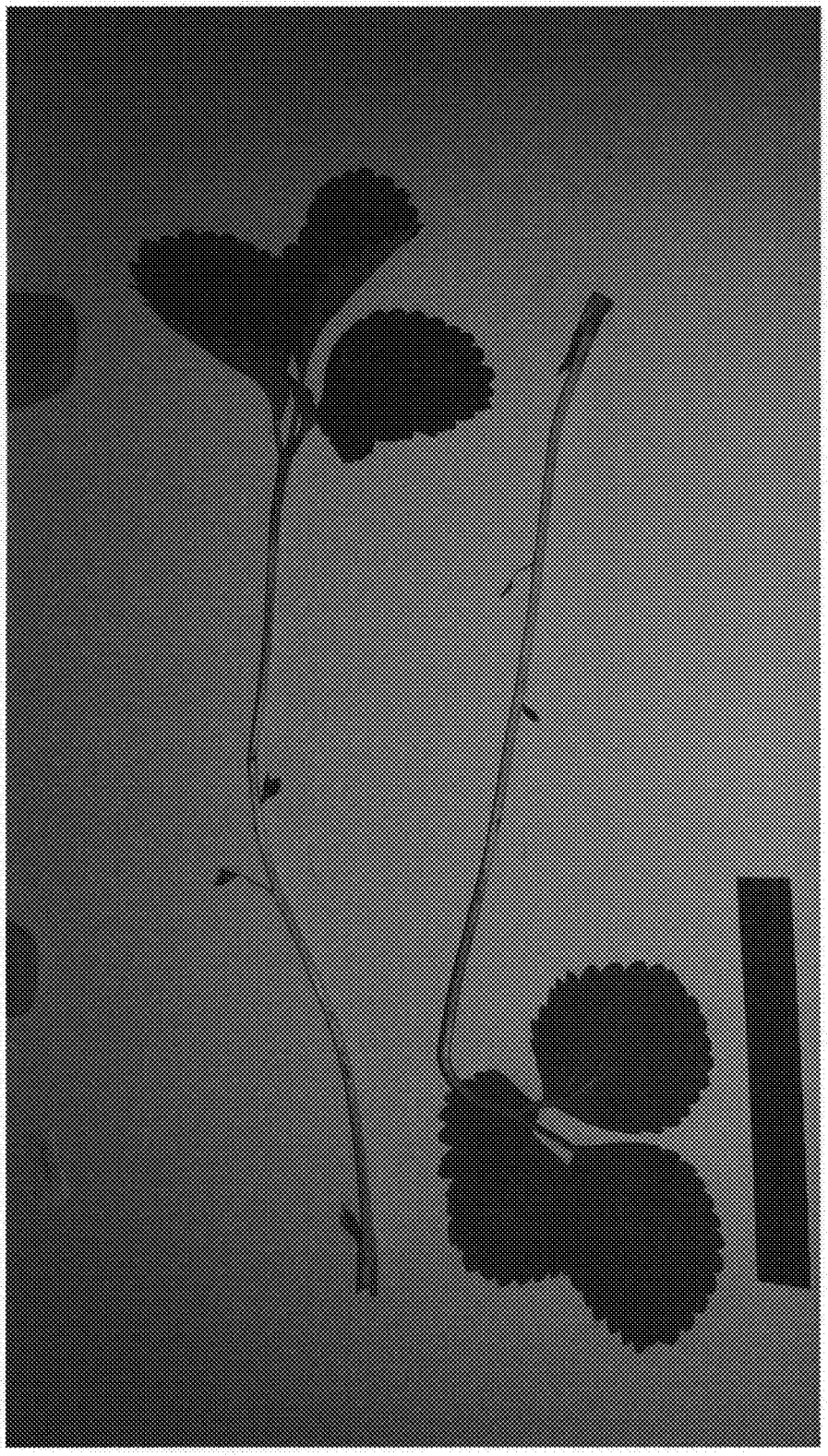
FIG. 4 shows 'Flame' plant leaves with petioles.
Figure 5:
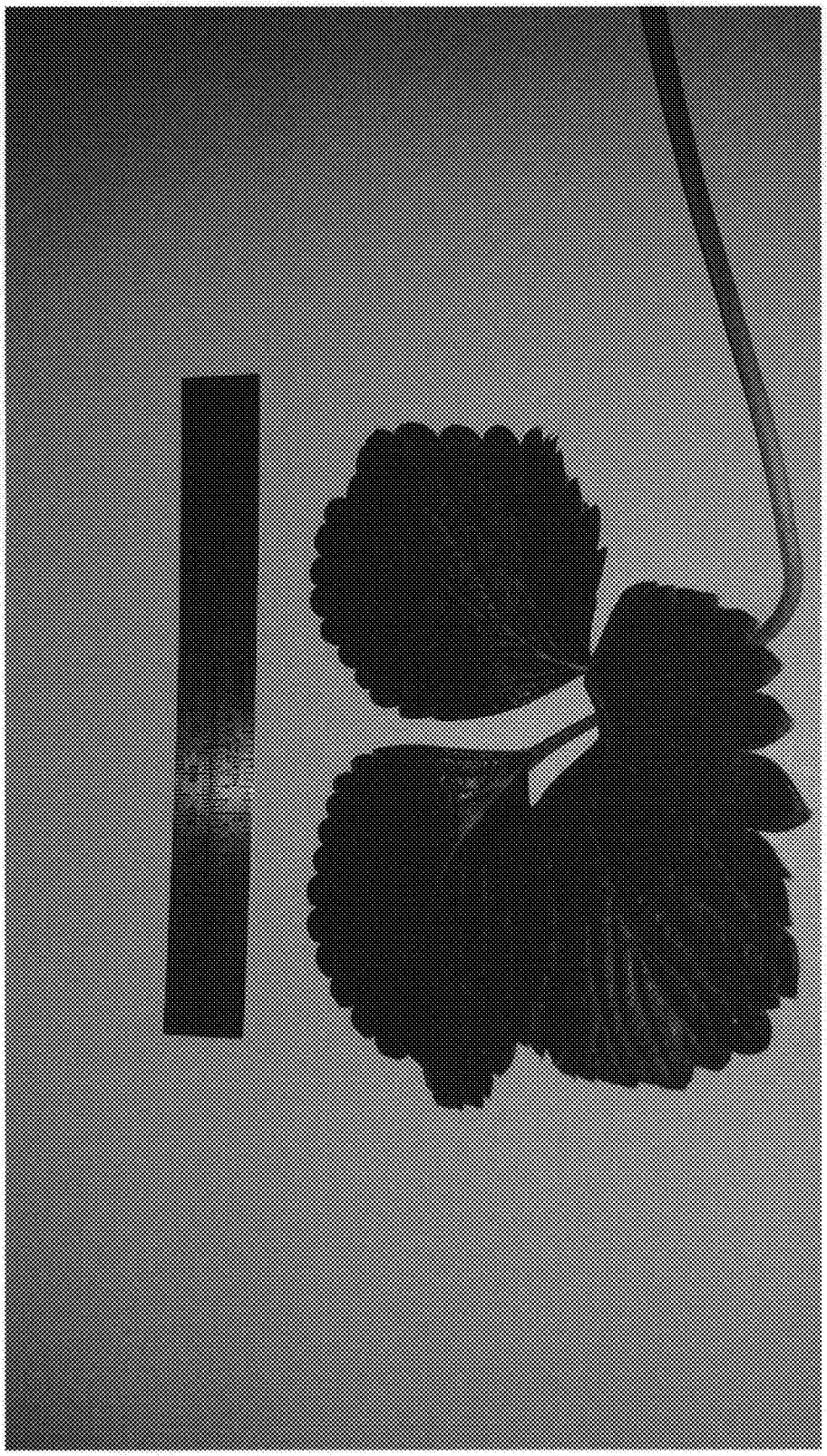
FIG. 5 shows a close-up look of a 'Flame' plant leaf.
Figure 6:
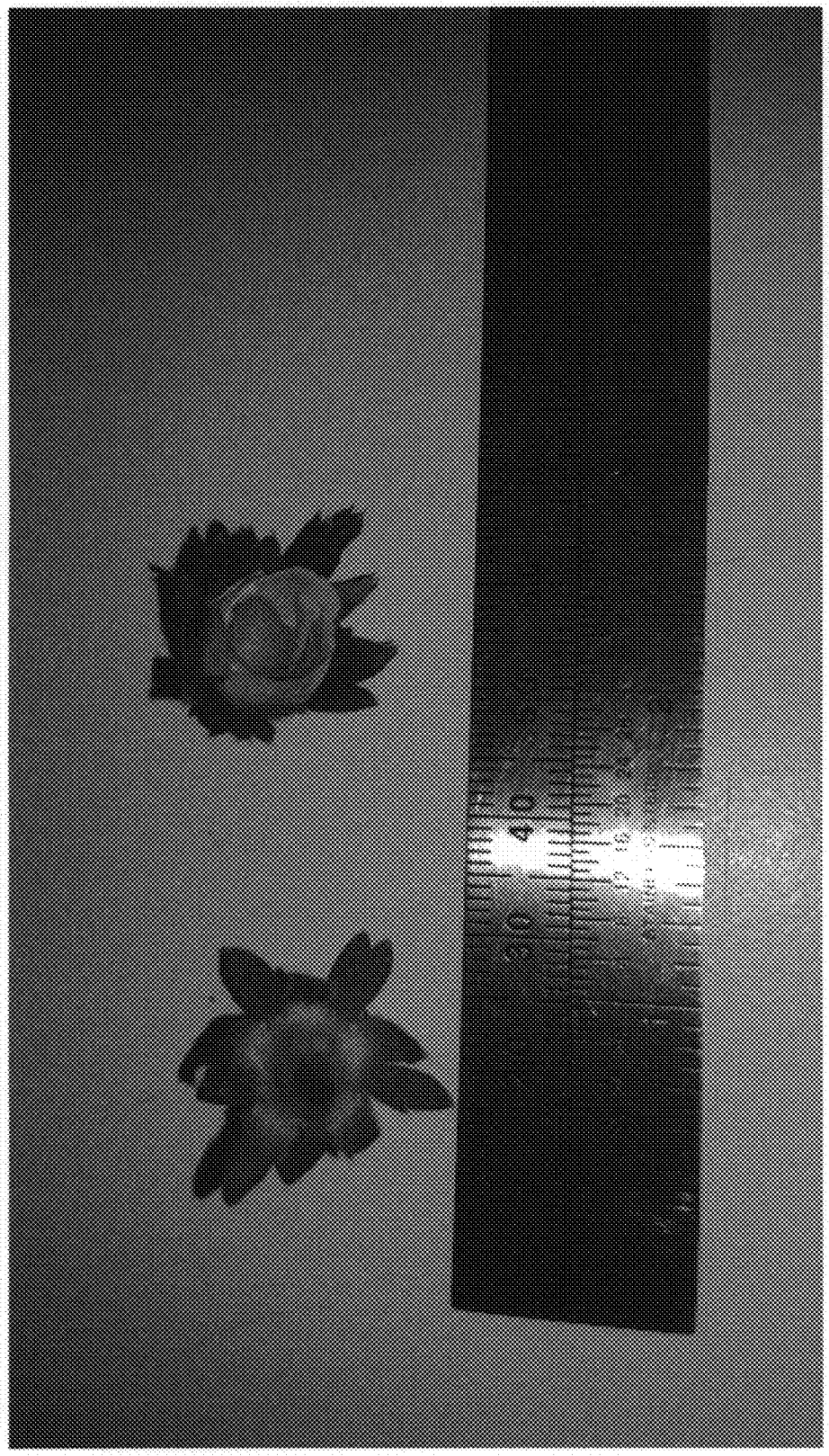
FIG. 6 shows flower petals and sepals of 'Flame' plant.

This invention relates to a new and distinctive day-neutral type cultivar designated as 'Flame'. It is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits in combination distinguish strawberry variety 'Flame' from the known strawberry varieties. Plants for the botanical measurements in the present application were grown as annuals. In the following description, color references are made to The Royal Horticultural Society Colour Chart, 1995 Edition, except where general terms of ordinary dictionary significance are used. Dormant bare root plants were planted on October, Year 1, and measurements in the table below were taken on November, Year 2.

'Flame' has not been observed under all possible environmental conditions, and the phenotype may vary significantly with variations in environment. The following observations, measurements, and comparisons describe this plant as grown under normal conditions in Watsonville, Calif. unless otherwise noted.

Hybrid Patent Data Sheet
(Dormant bare root plants were planted on October, Year 1, and measured on November, Year 2)
Variety: FLAME (A.K.A. '108229')

| Plant | |
|---|---|
| Plant Growth Habit | semi-upright |
| Day length | neutral |
| Planting season | fall |
| Density of foliage | light to medium |
| Average number of crowns per mature plant | 2 |
| Plant vigor | moderate |
| Rain/weather tolerance | moderate |
| Harvest Ease | easy |
| Height (mm) | 420 |
| Diameter (mm) | 495 (the entire plant structure, including the "superstructure" of petioles, leaves, flowers) 161 (inner "base" or "heart" structure of the plant, i.e. the mature apical and axial crowns of the strawberry plant where petioles, flowers and runners are attached) |
| **Terminal Leaf** | |
| Length (mm) | 87 |
| Width (mm) | 75 |
| Terminal leaflet length/width ratio | 1 |
| Blistering | none |
| Leaf glossiness | weak |
| No. teeth/terminal leaflet | 22 |
| shape of the terminal leaflet base | rounded |
| shape of terminal leaflet in cross-section | concave |
| margin description of the terminal | serrate to crenate |
| Shape of teeth | obtuse |
| Color of upper side of leaves | 136A |
| Color of lower side of leaves | 139C |
| presence or absence of any leaf variegation | absence |
| Number of leaflets | 33 |
| Terminal Leaflet margin | flat |
| Terminal Leaflet shape | orbicular |
| Terminal Leaflet shape of base | rounded |
| Terminal Leaflet shape of apex | rounded |
| **Petiole** | |
| Length (mm) | 34.1 |
| Width (mm) | 3.5 |
| Petiole pubescence | medium |
| Petiole pose of hairs | outwards |
| Petiole color | 145C |
| **Petiolule** | |
| Length (mm) | 30 |
| Width(mm) | 2 |

-continued

Hybrid Patent Data Sheet
(Dormant bare root plants were planted on October, Year 1, and measured on November, Year 2)
Variety: FLAME (A.K.A. '108229')

| Stolon | |
|---|---|
| Count (mm) | N/A |
| Diameter (mm) | N/A |
| Stolon color | 145A |
| Stolon anthocyanin | 187A |
| density of pubescence on the stolon | medium |
| Stolon number | 4 |
| Stolon thickness | medium |
| Stolon pubescence | medium |
| **Inflorescence** | |
| Petal/flower | 6 |
| **Inflorescence** | |
| position relative to foliage | even to above |
| flower arrangement of petals | touching |
| Number of flowers per plant | 30-40 |
| Flower size | medium |
| Corolla diameter (mm) | 11 |
| Calyx diameter (mm) | 15 |
| level of adherence of calyx | medium |
| Color of calyx | 137A |
| Pose of calyx segments | spreading |
| Petal length (mm) | 12 |
| Petal width (mm) | 9 |
| Petal length/width ratio | 1.3 |
| Petal shape | orbicular |
| Petal apex | rounded |
| Petal margin | entire |
| Petal base shape | concave |
| Petal spacing | overlapping |
| Petal color | 155C |
| Sepal length (mm) | 12 |
| Sepal width (mm) | 16 |
| Sepal shape | elliptical |
| Sepal apex | convex |
| Sepal margin | entire |
| Sepal number per flower | 20 |
| **Peduncle** | |
| **Stipules** | |
| Pedicel color | 145B |
| attitude of hairs on pedicel | upwards |
| Receptacle color | 150B |
| Fertility | self-fertile |
| Time of flowering | March |
| Anther color | 20A |
| Anther shape | NA |
| Anther size | NA |
| Number of stamen | 30 |
| Stamen length (mm) | NA |
| Number of pistils per flower | NA |
| Pistil length (mm) | NA |
| Shape of the stigma | NA |
| Stigma color | NA |
| Style color | NA |
| Style length (mm) | NA |
| Ovary color | NA |
| Pollen color | NA |
| Pollen amount | NA |
| Filament length | NA |
| Filament color | NA |
| **Fruit** | |
| Fruit/truss | 4 |
| Fruiting truss attitude | erect |
| Length (mm) | 50 |

-continued

Hybrid Patent Data Sheet
(Dormant bare root plants were planted on October, Year 1, and measured on November, Year 2)
Variety: FLAME (A.K.A. '108229')

| | |
|---|---|
| Width (mm) | 41 |
| Core length (mm) | 40 |
| Core width (mm) | 18 |
| Fruit skin color (color code) | 41A |
| Fruit weight (g) | 25 |
| Relative fruit size | medium |
| Predominant fruit shape | conical |
| Difference in shape between primary & secondary fruits | none to very slight |
| Fruit glossiness | medium |
| Position of achenes | even |
| Achenes per fruit | 136 |
| Achene weight (g) | 0.09 |
| Firmness | firm |
| Color of the flesh | 41A |
| Distribution of flesh color | entire |
| Time of fruit ripening | April |
| Harvest maturity (50% of plants with ripe fruit) | early |
| Type of bearing | Day neutral |
| Grams of fruit/plant (Peak season, June) | 912 |
| Appearance Score (from 1-5, with 5 = best) | 4 |
| Storage longevity | 7 to 10 days |
| Cull rate: Non salable fruit production rate | <10% |
| Disease and pest resistance: | Not tested |

(NA: not available)

When 'Flame' is compared to the proprietary female parent, 'Flame' has a lower height. The margin of the terminal leaf of 'Flame' is serrate to crenate, while the margin of the terminal leaf of the female parent is serrate.

When 'Flame' is compared to the proprietary male parent, 'Flame' has moderate plant vigor, while the male parent has high plant vigor.

When 'Flame' is compared to 'Seascape' (U.S. Plant Pat. No. 07,614), 'Flame' has a higher height. The margin of the terminal leaf of 'Flame' is serrate to crenate, while the margin of the terminal leaf of 'Seascape' is crenate. 'Flame' has fewer leaflets per plant when compared to 'Seascape'.

The invention claimed is:

1. A new and distinct cultivar of strawberry plant named 'Flame' substantially as shown and described herein.

* * * * *